US011358982B2

(12) United States Patent
Kumar

(10) Patent No.: US 11,358,982 B2
(45) Date of Patent: Jun. 14, 2022

(54) METHODS FOR THE IODINATION OF BIOMOLECULES

(71) Applicant: Ohio State Innovation Foundation, Columbus, OH (US)

(72) Inventor: Krishan Kumar, Powell, OH (US)

(73) Assignee: Ohio State Innovation Foundation, Columbus, OH (US)

(*) Notice: Subject to any disclaimer, the term of this patent is extended or adjusted under 35 U.S.C. 154(b) by 44 days.

(21) Appl. No.: 16/346,714

(22) PCT Filed: Nov. 1, 2017

(86) PCT No.: PCT/US2017/059503
§ 371 (c)(1),
(2) Date: May 1, 2019

(87) PCT Pub. No.: WO2018/085375
PCT Pub. Date: May 11, 2018

(65) Prior Publication Data
US 2019/0276490 A1    Sep. 12, 2019

Related U.S. Application Data

(60) Provisional application No. 62/415,871, filed on Nov. 1, 2016.

(51) Int. Cl.
| | | |
|---|---|---|
| *C07K 1/13* | (2006.01) | |
| *A61K 51/08* | (2006.01) | |
| *A61K 51/10* | (2006.01) | |
| *C07B 59/00* | (2006.01) | |
| *C07K 1/107* | (2006.01) | |
| *G01N 33/532* | (2006.01) | |

(52) U.S. Cl.
CPC .............. *C07K 1/13* (2013.01); *A61K 51/088* (2013.01); *A61K 51/1093* (2013.01); *C07B 59/008* (2013.01); *C07K 1/1072* (2013.01); *G01N 33/532* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,591,552 A | 5/1986 | Neurath | |
| 4,647,447 A | 3/1987 | Gries et al. | |
| 4,684,482 A | 8/1987 | Green | |
| 4,885,363 A | 12/1989 | Tweedle et al. | |
| 4,899,755 A | 2/1990 | Lauffer et al. | |
| 4,957,939 A | 9/1990 | Gries et al. | |
| 4,963,344 A | 10/1990 | Gries et al. | |
| 5,021,556 A | 6/1991 | Fujiritsu et al. | |
| 5,075,099 A | 12/1991 | Srinivasan et al. | |
| 5,118,797 A | 6/1992 | Jurisson et al. | |
| 5,183,653 A | 2/1993 | Linder et al. | |
| 5,364,613 A | 11/1994 | Sieving et al. | |
| 5,367,080 A | 11/1994 | Toner et al. | |
| 5,387,409 A | 2/1995 | Nunn et al. | |
| 5,424,402 A | 6/1995 | Hussain et al. | |
| 5,474,756 A | 12/1995 | Tweedle et al. | |
| 5,608,110 A | 3/1997 | Ramalingam et al. | |
| 5,656,254 A | 8/1997 | Ramalingam et al. | |
| 5,662,885 A | 9/1997 | Pollak et al. | |
| 5,665,329 A | 9/1997 | Ramalingam et al. | |
| 5,688,487 A | 11/1997 | Linder et al. | |
| 5,720,934 A | 2/1998 | Dean et al. | |
| 5,780,006 A | 7/1998 | Pollak et al. | |
| 5,846,519 A | 12/1998 | Tweedle et al. | |
| 5,886,142 A | 3/1999 | Thakur et al. | |
| 5,976,495 A | 11/1999 | Pollak et al. | |
| 5,985,239 A * | 11/1999 | Hussain | A01N 37/12 424/1.11 |
| 6,093,382 A | 7/2000 | Wedeking et al. | |
| 6,143,274 A | 11/2000 | Tweedle et al. | |
| 8,309,583 B2 | 11/2012 | Codd et al. | |
| 2005/0277197 A1 | 12/2005 | Chandler et al. | |
| 2014/0295568 A1 | 10/2014 | Evtodienko et al. | |

FOREIGN PATENT DOCUMENTS

| | | |
|---|---|---|
| WO | WO 86/06605 | 11/1986 |
| WO | WO 91/03200 | 3/1991 |
| WO | WO95/03280 | 2/1995 |
| WO | WO95/06633 | 3/1995 |
| WO | WO 95/28179 | 10/1995 |

(Continued)

OTHER PUBLICATIONS

Ferens et al. "High-level Iodination of Monoclonal Antibody Fragments for Radiotherapy" J. Nucl. Med. 25:367-370. (Year: 1984).*
Anonymous "Basic Information About Chloramines" (Year: 2009).*
Svensson et al. "Therapeutic Effects of Monoclonal Antibody-B-Lactamase Conjugates in Combination with a Nitrogen Mustard Anticancer Prodrug in Models of Human Renal Cell Carcinoma" J. Med. Chem. 41:1507-1512. (Year: 1998).*
Lane D and Richardson D "Revolutions in the labelling of proteins with radionuclides of iodine William Hunter and radioiodination" Biochemical J. 33:34-38. (Year: 2011).*
Extended European Search Report issued by the European Patent Office in Application No. EP 17866727.5 dated May 26, 2020. 7 pages.

(Continued)

*Primary Examiner* — Sudhakar Katakam
*Assistant Examiner* — Zachary J Miknis
(74) *Attorney, Agent, or Firm* — Meunier Carlin & Curfman LLC

(57) ABSTRACT

Provided herein are methods for iodinating biomolecules, including proteins and peptides. The methods can be used to successfully and efficiently iodinate biomolecules under relatively mild reaction conditions. As a consequence, the methods described herein can be used to iodinate biomolecules that include, for example, an oxidatively unstable moiety (e.g., an optical dye) without adversely impacting the oxidatively unstable moiety.

15 Claims, 2 Drawing Sheets

(56) References Cited

FOREIGN PATENT DOCUMENTS

| WO | WO96/03427 | 2/1996 |
| --- | --- | --- |
| WO | WO 96/23526 | 8/1996 |
| WO | WO 97/36619 | 10/1997 |
| WO | WO 98/18496 | 5/1998 |
| WO | WO98/46612 | 10/1998 |
| WO | WO99/17809 | 4/1999 |

OTHER PUBLICATIONS

Seevers, Robert H., and Raymond E. Counsell. "Radioiodination techniques for small organic molecules." Chemical reviews 82.6 (1982): 575-590.
International Search Report and Written Opinion. Issued by the International Searching Authority (US) in PCT Application No. PCT/US2017/059503 dated Jan. 23, 2018. 9 pages.
Bailey, GS; Radioisotopes in Biology (Slater, RJ ed), IRL, Oxford, UK, p. 195.
Caravan, Peter, et al. "Gadolinium (III) chelates as MRI contrast agents: structure, dynamics, and applications." Chemical reviews 99.9 (1999): 2293-2352.
Fraker, Pamela J., and John C. Speck Jr. "Protein and cell membrane iodinations with a sparingly soluble chloroamide, 1, 3, 4, 6-tetrachloro-3a, 6a-diphenylglycoluril." Biochemical and biophysical research communications 80.4 (1978): 849-857.
Greenwood, FC; Hunter, WM; Glover, JS; The preparation of 131I-labelled human growth hormone of high specific radioactivity. Biochem Journal, 89, 114 (1963).
Kumar, Krishan, Richard A. Day, and Dale W. Margerum. "Atom-transfer redox kinetics: general-acid-assisted oxidation of iodide by chloramines and hypochlorite." Inorganic Chemistry 25.24 (1986): 4344-4350.
Lee, Ch Y., and R. J. Ryan. "Interaction of ovarian receptors with human luteinizing hormone and human chorionic gonadotropin." Biochemistry12.23 (1973): 4609-4615.
Liu, Shuang, and D. Scott Edwards. "99mTc-labeled small peptides as diagnostic radiopharmaceuticals." Chemical reviews 99.9 (1999): 2235-2268.
Markwell, Mary Ann K., and C. Fred Fox. "Surface-specific iodination of membrane proteins of viruses and eucaryotic cells using 1, 3, 4, 6-tetrachloro-3α, 6α-diphenylglycoluril." Biochemistry 17.22 (1978): 4807-4817.
Salacinski, Philip RP, et al. "Iodination of proteins, glycoproteins, and peptides using a solid-phase oxidizing agent, 1, 3, 4, 6-tetrachloro-3α, 6α-diphenyl glycoluril (Iodogen)." Analytical biochemistry 117.1 (1981): 136-146.
International Preliminary Report on Patentability issued for Application No. PCT/US2017/059503, dated May 16, 2019.

* cited by examiner

METHODS FOR THE IODINATION OF BIOMOLECULES

CROSS-REFERENCE TO RELATED APPLICATIONS

This application is a national stage application filed under 35 U.S.C. § 371 of PCT/US2017/059503 filed Nov. 1, 2017, which claims the benefit of priority to U.S. Provisional Application 62/415,871, filed Nov. 1, 2016, which is incorporated by reference herein in its entirety.

STATEMENT OF GOVERNMENT SUPPORT

This invention was made with government support under grant number CA176664 awarded by the National Institutes of Health. The government has certain rights in the invention.

BACKGROUND

Radioiodinated peptides and proteins play an important role in a variety of therapeutic and diagnostic applications. As a consequence, a number of methods have been developed over the last thirty years to chemically introduce radioiodine into proteins and peptides. Iodine is preferred as a radiolabel in these applications because the chemistry used for radioiodination is relatively straightforward, radioiodine has useful physical decay characteristics, and isotopes of iodine are commercially available. Useful iodine isotopes include iodine-123 and iodine-125, both of which are gamma-emitting isotopes that are used for Single-Photon Emission Computed Tomography (SPECT), iodine-124, which is used as a radiotracer in Positron Emission Tomography (PET), and iodine-131, which is widely used for radioimmunotherapy.

Various chemistries have been developed to incorporate iodine isotopes in proteins and peptides for use in these applications. The most common linking procedure has been to prepare in situ an electrophilic radioiodine species to react with a functional group on an antibody. Reagents such as chloramine T, iodobeads, and iodogen have been employed to generate electrophilic iodine. However, these reagents have the potential to adversely impact the protein or peptide as well as other oxidatively sensitive moieties that may be present. These reagents can also produce undesirable N-chloro derivatives. Accordingly, improved methods for iodinating proteins and peptides that employ milder conditions are needed.

SUMMARY

Provided herein are methods for iodinating biomolecules, including proteins and peptides. The methods can be used to successfully and efficiently iodinate biomolecules under relatively mild reaction conditions. As a consequence the methods described herein can be used to iodinate biomolecules that include, for example, an oxidatively unstable moiety (e.g., an optical dye) without adversely impacting the oxidatively unstable moiety.

Methods for iodinating biomolecules can comprise providing a biomolecule comprising a tyrosine residue; and reacting the biomolecule with a chloramine and an iodine source under conditions effective to form an iodinated biomolecule. The resulting iodinated biomolecule can comprise an iodinated tyrosine residue.

The chloramine can be any suitable chloramine that is compatible with the methods described herein. In some embodiments, the chloramine can comprise an organic chloramine. In some of these cases, the organic chloramine can be a non-aromatic chloramine (i.e., the chloramine does not include an aromatic moiety, such as a phenyl group). For example, the organic chloramine can comprise an alkylchloramine, such as methylchloramine, dimethylchloramine, ethylchloramine, diethylchloramine, or a combination thereof. In other embodiments, the organic chloramine can comprise an N-chloro amino acid. The N-chloro amino acid can comprise an N-monochloro amino acid or an N-dichloro amino acid, such as glycine, lysine, alanine, leucine, isoleucine, serine, glutamine, etc. In other embodiments, the organic chloramine can comprise an N-chloro peptide, such as an N-monochloro or an N-dichloro derivative of an oligopeptide such diglycine, alanylalanine, or glycylalanaine. In other embodiments, the chloramine can comprise an inorganic chloramine, such as monochloramine, dichloramine, trichloramine, or a combination thereof.

In some embodiments, the chloramine can have a molar mass of less than 250 g/mol (e.g., less than 200 g/mol, less than 150 g/mol, or less than 100 g/mol). In certain embodiments, the chloramine can have a molar mass of from 50 g/mol to 250 g/mol (e.g., from 50 g/mol to 200 g/mol, from 50 g/mol to 150 g/mol, or from 50 g/mol to 100 g/mol). In certain embodiments, the chloramine can comprise monochloramine.

The iodine source can comprise any suitable iodine source. Appropriate iodine sources can be selected in view of a number of factors, including the desired isotope of iodine to be incorporated into the iodinated biomolecule. In some cases, the iodine source can include isotope that undergoes beta decay (e.g., beta minus decay or beta plus decay). In some cases, the iodine source can include isotope that undergoes gamma decay. For example, in some embodiments, the iodine source can include $^{123}$I, $^{124}$I, $^{125}$I, or $^{131}$I. In certain embodiments, the iodine source can comprise an iodide salt (e.g., an alkali metal salt), such as sodium iodide or potassium iodide. For example, the iodide salt can comprise [$^{123}$I] NaI, [$^{124}$I] NaI, [$^{125}$I] NaI, [$^{131}$I] NaI, [$^{123}$I] KI, [$^{124}$I] KI, [$^{125}$I] KI, or [$^{131}$I] KI.

In some embodiments, the methods for iodinating biomolecules can further comprise reacting ammonia or an alkylamine, an amino acid comprising a primary amine, or a peptide comprising a primary amine with hypochlorite under conditions effective to form the chloramine. In these embodiments, the molar ratio of the ammonia or alkylamine and the hypochlorite can be from 0.8:1 to 3:1 (e.g., from 0.8:1 to 2:1, from 0.8:1 to 1.5:1, or from 0.8:1 to 1.2:1). In certain embodiments, the molar ratio of the ammonia or alkylamine and the hypochlorite can be about 1:1.

The iodinated tyrosine residue can be defined by Formula IA or Formula IB below

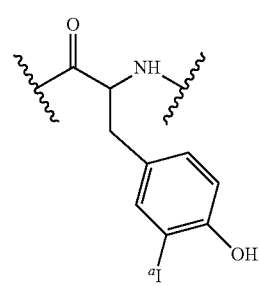

Formula IA

Formula IB

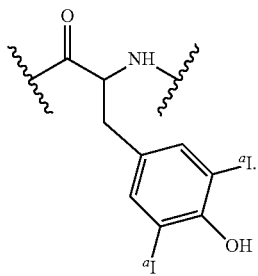

In some of these embodiments, $^aI$ can be chosen from $^{123}I$, $^{124}I$, $^{125}I$, and $^{131}I$.

In certain embodiments, the biomolecule can be defined by the formula below

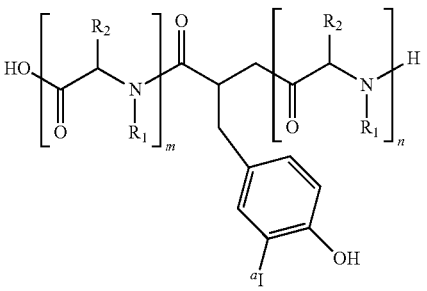

and the iodinated biomolecule can be defined by Formula IIA or Formula IIB below Formula IIA

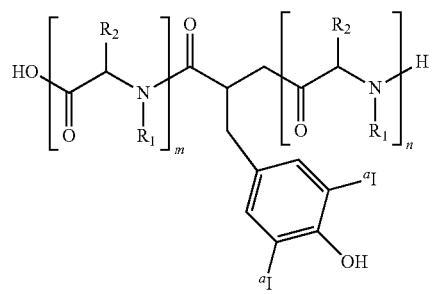

Formula IIB

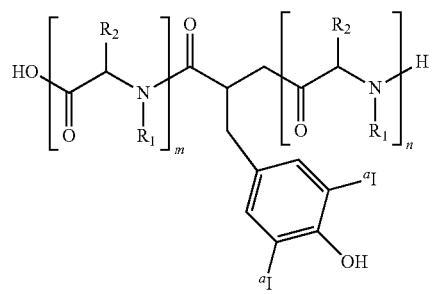

wherein m is an integer from 0 to 150 and n is an integer from 0 to 150, with the proviso that at least one of m and n is not 0; and independently for each occurrence in the polypeptide, $R_1$ is H and $R_2$ is selected from one of the following

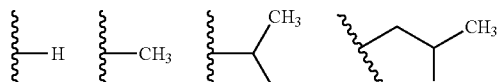

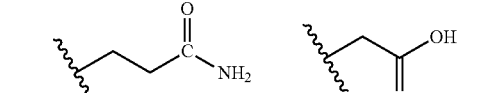

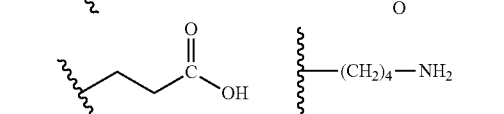

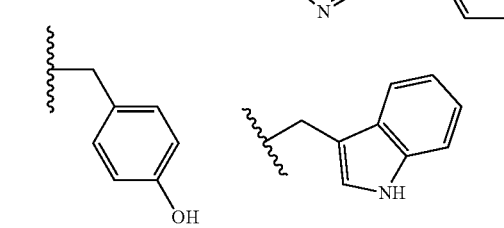

or $R_1$ and $R_2$, together with the atoms to which they are attached, form a five-membered heterocycle defined by the structure below

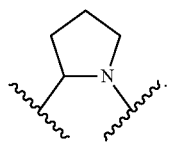

In some of these embodiments, $^aI$ can be chosen from $^{123}I$, $^{124}I$, $^{125}I$, and $^{131}I$. In some embodiments, the biomolecule can comprise an antibody or antibody fragment. In some embodiments, the biomolecule can comprise a therapeutic peptide or protein.

As discussed above, the methods described herein can be used to iodinate biomolecules that include, for example, an oxidatively unstable moiety (e.g., an optical dye) without adversely impacting the oxidatively unstable moiety. Accordingly, in some embodiments, the biomolecule can further comprise an oxidatively unstable moiety, and the oxidatively unstable moiety remains intact following the reaction step such that the iodinated biomolecule also includes the oxidatively unstable moiety (e.g., a group that includes a conjugated moiety). The oxidatively unstable moitety can comprise, for example, a chromophore, fluorophore, metal chelator, or combinations thereof. Accordingly, the methods described herein can be used to create dual-function probes (e.g., biomolecules that include both an iodine radionuclide and a second functional group, such as an optical dye).

DETAILED DESCRIPTION

Figure 1:
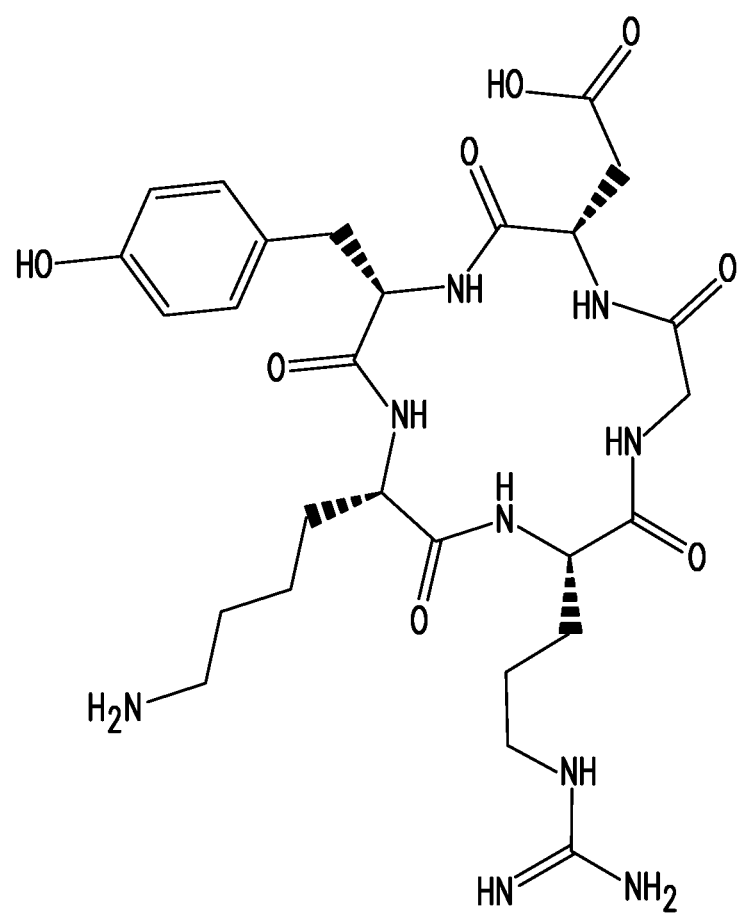
FIG. 1 illustrates the structure of cRGDyK (cyclo Arg-Gly-Asp-d-Tyr-Lys).

Provided herein are methods for iodinating biomolecules, including proteins and peptides. The methods can be used to successfully and efficiently iodinate biomolecules under milder reaction conditions. As a consequence the methods described herein can be used to iodinate biomolecules that include, for example, an oxidatively unstable moiety (e.g., an optical dye) without adversely impacting the oxidatively unstable moiety. For example, the methods described herein can be used to iodinate biomolecules that are conjugated to an oxidatively unstable molecule, such as an optical dye, without adversely impacting the oxidatively unstable molecule.

Methods for iodinating biomolecules can comprise reacting a biomolecule comprising a tyrosine residue with a chloramine and an iodine source under conditions effective to form an iodinated biomolecule. The resulting iodinated biomolecule can comprise an iodinated tyrosine residue.

The chloramine can be any suitable chloramine that is compatible with the methods described herein. The chloramine can be a low molecular weight chloramine. For example, in some embodiments, the chloramine can have a molar mass of less than 250 g/mol (e.g., less than 225 g/mol, less than 200 g/mol, less than 175 g/mol, less than 150 g/mol, less than 125 g/mol, less than 100 g/mol, less than 90 g/mol, less than 80 g/mol, less than 70 g/mol, or less than 60 g/mol). In some embodiments, the chloramine can have a molar mass of at least 50 g/mol (e.g., at least 60 g/mol, at least 70 g/mol, at least 80 g/mol, at least 90 g/mol, at least 100 g/mol, at least 125 g/mol, at least 150 g/mol, at least 175 g/mol, at least 200 g/mol, or at least 225 g/mol).

The chloramine can have a molar mass ranging from any of the minimum values described above to any of the maximum values described above. For example, in some embodiments, the chloramine can have a molar mass of from 50 g/mol to 250 g/mol (e.g., from 50 g/mol to 200 g/mol, from 50 g/mol to 150 g/mol, or from 50 g/mol to 100 g/mol).

In some embodiments, the chloramine can comprise an organic chloramine. In some of these cases, the organic chloramine can be a non-aromatic chloramine (i.e., the chloramine does not include an aromatic moiety, such as a phenyl group). For example, the organic chloramine can comprise an alkylchloramine, such as methylchloramine, dimethylchloramine, ethylchloramine, diethylchloramine, or a combination thereof. In other embodiments, the organic chloramine can comprise an N-chloro amino acid. The N-chloro amino acid can comprise an N-monochloro amino acid or an N-dichloro amino acid. The N-chloro amino acid can be an N-chlorinated derivative of any suitable amino acid, such as a proteinogenic amino acid (e.g., glycine, alanine, valine, leucine, isoleucine, serine, cysteine, threonine, methionine, proline, phenylalanine, tyrosine, tryptophan, histidine, lysine, arginine, aspartic acid, glutamic acid, asparagine, glutamine, or a combination thereof) or a non-proteinogenic amino acid. The N-chloro amino acid can be an N-chlorinated derivative of glycine, lysine, alanine, leucine, isoleucine, serine, or glutamine.

In other embodiments, the organic chloramine can comprise an N-chloro peptide. The N-chloro peptide can comprise an N-monochloro peptide or an N-dichloro peptide. The N-chloro peptide can be an N-chlorinated derivative of any suitable peptide containing one or more primary amine groups. In some embodiments, the N-chloro peptide can comprise from 2 to 20 amino acid residues (e.g., from 2 to 15 amino acid residues, 2 to 10 amino acid residues, or 2 to 5 amino acid residues). For example, in some embodiments, the N-chloro peptide can be an N-monochloro or an N-dichloro derivative of an oligopeptide such diglycine, alanylalanine, or glycylalanaine. In other embodiments, the chloramine can comprise an inorganic chloramine, such as monochloramine, dichloramine, trichloramine, or a combination thereof. In certain embodiments, the chloramine can comprise monochloramine.

The iodine source can comprise any suitable iodine source. Appropriate iodine sources can be selected in view of a number of factors, including the desired isotope of iodine to be incorporated into the iodinated biomolecule. In some cases, the iodine source can include isotope that undergoes beta decay (e.g., beta minus decay or beta plus decay). In some cases, the iodine source can include isotope that undergoes gamma decay. For example, in some embodiments, the iodine source can include $^{123}I$, $^{124}I$, $^{125}I$, or $^{131}I$. If desired for a particular application, other iodine isotopes, such as $^{126}I$ can be used.

In certain embodiments, the iodine source can comprise an iodide salt (e.g., an alkali metal salt), such as sodium iodide or potassium iodide. For example, the iodide salt can comprise [$^{123}I$] NaI, [$^{124}I$] NaI, [$^{125}I$] NaI, [$^{131}I$] NaI, [$^{123}I$] KI, [$^{124}I$] KI, [$^{125}I$] KI, or [$^{131}I$] KI.

In some embodiments, the methods for iodinating biomolecules can further comprise reacting ammonia or an alkylamine, an amino acid comprising a primary amine, or a peptide comprising a primary amine with hypochlorite under conditions effective to form the chloramine. In these embodiments, the molar ratio of the ammonia or alkylamine and the hypochlorite can be from 0.8:1 to 3:1 (e.g., from 0.8:1 to 2:1, from 0.8:1 to 1.5:1, or from 0.8:1 to 1.2:1). In certain embodiments, the molar ratio of the ammonia or alkylamine and the hypochlorite can be about 1:1.

The iodinated tyrosine residue can be defined by Formula IA or Formula IB below

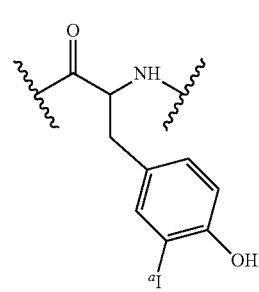

Formula IA

Formula IB

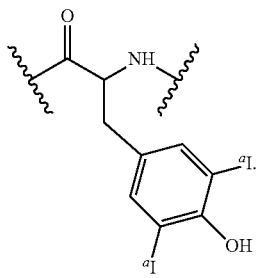

In some of these embodiments, $^aI$ can be chosen from $^{123}I$, $^{124}I$, $^{125}I$, and $^{131}I$.

The biomolecule can comprise any protein or peptide. The term "peptide," as used herein, refers to a chain of at least two amino acids attached to one another by a peptide bond. In some embodiments, a peptide may include at least 3-5 amino acids, each of which is attached to others by way of at least one peptide bond. The peptides can be naturally occurring or synthetic, linear as well as cyclic. The term "peptide" embraces the term "polypeptide", which as used herein, refers to a long, continuous, and unbranched peptide chain containing about 10 to about 100 amino acids or more.

The term "peptide" encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C— terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), a-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

The term "protein" as used herein refers to a macromolecule containing more than 100 amino acids attached to one another by a peptide bond. Proteins contain one or more polypeptides, for example linked by one or more disulfide bonds or associated by other means, and may include moieties other than amino acids (e.g., may be glycoproteins, proteoglycans, etc.) and/or may be otherwise processed or modified. A "protein" can be a complete polypeptide chain as produced by a cell (with or without a signal sequence), or can be a characteristic portion thereof. Proteins may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

In some cases, the biomolecule can comprise a therapeutic peptide or protein. Therapeutic peptides and proteins include bioactive peptides and proteins that have therapeutic utility. Illustrative categories of therapeutic peptides and proteins include hormones, antibodies, aptamers, extracellular matrix (ECM) peptides, soluble receptors, decoys, fusion proteins, enzymes, cytokines and the like.

In certain embodiments, the biomolecule comprises an antibody. The term "antibody" refers to natural or synthetic antibodies that selectively bind a target antigen. The term includes polyclonal and monoclonal antibodies. In addition to intact immunoglobulin molecules, also included in the term "antibodies" are antibody fragments or polymers of those immunoglobulin molecules, and human or humanized versions of immunoglobulin molecules that selectively bind the target antigen. The term encompasses intact and/or full length immunoglobulins of types IgA, IgG (e.g., IgG1, IgG2, IgG3, IgG4), IgE, IgD, IgM, IgY, antigen-binding fragments and/or single chains of complete immunoglobulins (e.g., single chain antibodies, Fab fragments, F(ab')2 fragments, Fd fragments, scFv (single-chain variable), and single-domain antibody (sdAb) fragments), and other proteins that include at least one antigen-binding immunoglobulin variable region, e.g., a protein that comprises an immunoglobulin variable region, e.g., a heavy (H) chain variable region (VH) and optionally a light (L) chain variable region (VL). The light chains of an antibody may be of type kappa or lambda.

An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

In certain embodiments, the biomolecule can be defined by the formula below

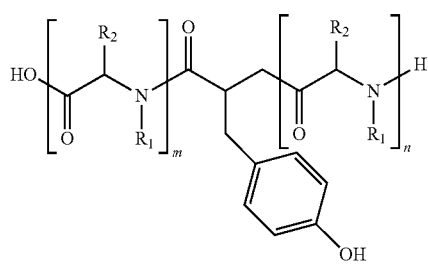

and the iodinated biomolecule can be defined by Formula IIA or Formula IIB below

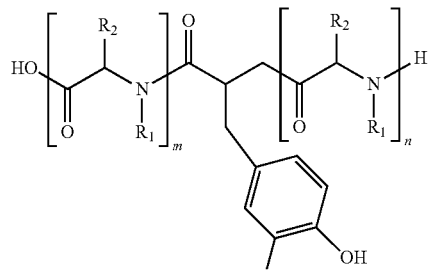

Formula IIA

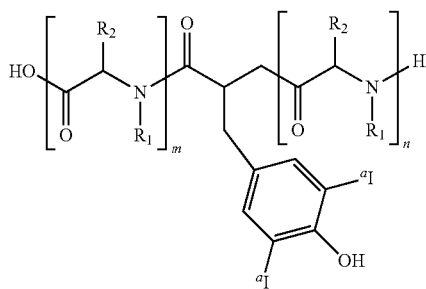

Formula IIB wherein m is an integer from 0 to 150 and n is an integer from 0 to 150, with the proviso that at least one of m and n is not 0; and independently for each occurrence in the polypeptide, $R_1$ is H and $R_2$ is selected from one of the following

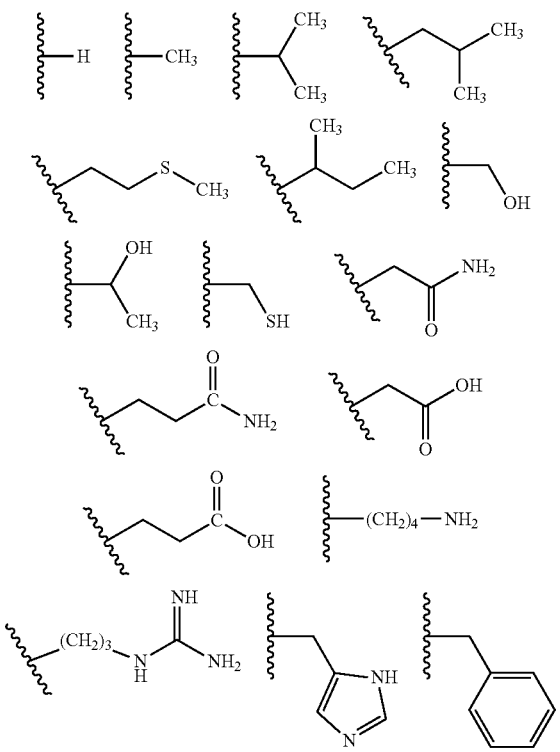

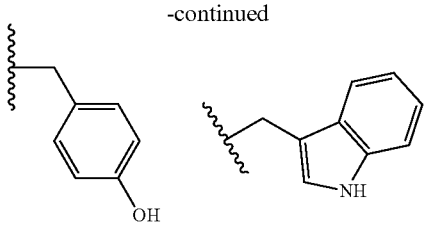

or $R_1$ and $R_2$, together with the atoms to which they are attached, form a five-membered heterocycle defined by the structure below

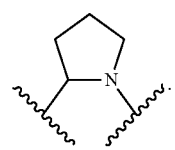 [SMILES: *C1CCCN1*]

In some of these embodiments, $^aI$ can be chosen from $^{123}I$, $^{124}I$, $^{125}I$, and $^{131}I$. In some embodiments, the biomolecule can comprise an antibody or antibody fragment. In some embodiments, the biomolecule can comprise a therapeutic peptide or protein.

In some embodiments, m can be at least 1 (e.g., at least 5, at least 10, at least 20, at least 30, at least 40, at least 50, at least 60, at least 70, at least 80, at least 90, at least 100, at least 110, at least 120, at least 130, or at least 140). In some embodiments, m can be 150 or less (e.g., 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). m can be an integer ranging from any of the minimum values described above to any of the maximum values described above. For example, in some embodiments, m can be an integer from 1 to 150 (e.g., from 1 to 100, from 1 to 50, from 1 to 30, or from 1 to 10).

In some embodiments, n can be at least 1 (e.g., at least 5, at least 10, at least 20, at least 30, at least 40, at least 50, at least 60, at least 70, at least 80, at least 90, at least 100, at least 110, at least 120, at least 130, or at least 140). In some embodiments, n can be 150 or less (e.g., 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). n can be an integer ranging from any of the minimum values described above to any of the maximum values described above. For example, in some embodiments, n can be an integer from 1 to 150 (e.g., from 1 to 100, from 1 to 50, from 1 to 30, or from 1 to 10).

In some embodiments, the sum of m and n can be at least 1 (e.g., at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, or at least 290). In some embodiments, the sum of m and n can be 300 or less (e.g., 290 or less, 280 or less, 270 or less, 260 or less, 250 or less, 240 or less, 230 or less, 220 or less, 210 or less, 200 or less, 190 or less, 180 or less, 170 or less, 160 or less, 150 or less, 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). The sum of m and n can range from any of the minimum values described above to any of the maximum values described above. For example, in some embodiments, the sum of m and n can be from 1 to 300 (e.g., from 1 to 150, from 1 to 100, from 1 to 50, from 1 to 30, from 1 to 10, from 5 to 300, from 5 to 150, from 5 to 100, from 5 to 50, from 5 to 30, or from 5 to 10).

While the biomolecules described above are envisioned as substrates for the methods of iodination described herein, the methods can in principle be used to radioiodinate any organic compound or biomolecule containing an activated phenyl group (e.g., a phenyl group that includes an electron donating group, such as —OH, —$NH_2$, —NHR, —$NR_2$ attached to the phenyl ring).

As discussed above, the methods described herein can be used to iodinate biomolecules that include, for example, an oxidatively unstable moiety (e.g., an optical dye) without adversely impacting the oxidatively unstable moiety. Accordingly, in some embodiments, the biomolecule can further comprise an oxidatively unstable moiety, and the oxidatively unstable moiety remains intact following the reacting step such that the iodinated biomolecule also includes the oxidatively unstable moiety (e.g., a group that includes a conjugated moiety). The oxidatively unstable moiety can be a moiety that is stable for less than 15 minutes (e.g., less than 10 minutes, or less than 5 minutes) when dissolved in Tris iodination buffer and incubated in a Pierce® Pre-Coated Iodination Tube and NaI at room temperature. The oxidatively unstable moitety can comprise, for example, a chromophore, fluorophore, metal chelator, or combinations thereof. Accordingly, the methods described herein can be used to create dual-function probes (e.g., biomolecules that include both an iodine radionuclide and a second functional group, such as an optical dye).

In some embodiments, the oxidatively unstable moiety can be a moiety that is detectable in the body of a subject by an imaging technique such as X-ray radiography, ultrasound, computed tomography (CT), single-photon emission computed tomography (SPECT), magnetic resonance imaging (MRI), positron emission tomography (PET), Optical Fluorescent Imaging, Optical Visible light imaging, and nuclear medicine including Cerenkov Light Imaging.

In some embodiments, the oxidatively unstable moitety can be a metal chelator. The terms "metal chelator" and "chelating agent" refer to a polydentate ligand that can form a coordination complex with a metal atom. It is generally preferred that the coordination complex is stable under physiological conditions. That is, the metal will remain complexed to the chelator in vivo.

In some cases, the metal chelator is a molecule that complexes to a radionuclide metal or paramagnetic metal ion to form a metal complex that is stable under physiological conditions. The metal chelator may be any of the metal chelators known in the art for complexing a medically useful paramagnetic metal ion, or radionuclide.

In some cases, such as in the case of certain biomolecules designed for radiopharmaceutical or radiotherapy applications, it can be convenient to prepare the complexes comprising a radionuclide, at or near the site where they are to be used (e.g., in a hospital pharmacy or clinic). Accordingly, in some embodiments, the biomolecule can comprise a metal chelator uncomplexed with a metal ion. In such embodiments, the biomolecule can be complexed with a suitable metal ion prior to administration. In other embodiments, the biomolecule can comprise a metal chelator complexed with a suitable metal ion (e.g., a paramagnetic metal ion or a radionuclide).

Suitable metal chelators include, for example, linear, macrocyclic, terpyridine, and $N_3S$, $N_2S_2$, or $N_4$ chelators (see also, U.S. Pat. Nos. 4,647,447, 4,957,939, 4,963,344, 5,367,080, 5,364,613, 5,021,556, 5,075,099, 5,886,142, the disclosures of which are incorporated by reference herein in their entirety), and other chelators known in the art including, but not limited to, HYNIC, DTPA, EDTA, DOTA, TETA, and bisamino bisthiol (BAT) chelators (see also U.S. Pat. No. 5,720,934). For example, macrocyclic chelators, and in particular $N_4$ chelators are described in U.S. Pat. Nos. 4,885,363; 5,846,519; 5,474,756; 6,143,274; 6,093,382; 5,608,110; 5,665,329; 5,656,254; and 5,688,487, the disclosures of which are incorporated by reference herein in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference herein in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, Chem. Rev. 1999, 99, 2235-2268; Caravan et al., Chem. Rev. 1999, 99, 2293-2352; and references therein, the disclosures of which are incorporated by reference herein in their entirety.

The metal chelator may also include complexes known as boronic acid adducts of technetium and rhenium dioximes, such as those described in U.S. Pat. Nos. 5,183,653; 5,387,409; and 5,118,797, the disclosures of which are incorporated by reference herein, in their entirety.

Examples of suitable chelators include, but are not limited to, derivatives of diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 tetraazacyclododecane triacetic acid (DO3A), derivatives of the 1-1-(1-carboxy-3-(p-nitrophenyl)propyl-1,4,7,10 tetraazacyclododecane triacetate (PA-DOTA) and MeO-DOTA, ethylenediaminetetraacetic acid (EDTA), and 1,4,8,11-tetraazacyclotetradecane-1,4,8,11-tetraacetic acid (TETA), derivatives of 3,3,9,9-Tetramethyl-4,8-diazaundecane-2,10-dione dioxime (PnAO); and derivatives of 3,3,9,9-Tetramethyl-5-oxa-4,8-diazaundecane-2,10-dione dioxime (oxa PnAO). Additional chelating ligands are ethylenebis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl-DTPA; bis-2 (hydroxybenzyl)-ethylene-diaminediacetic acid (HBED) and derivatives thereof; the class of macrocyclic compounds which contain at least 3 carbon atoms and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl)aminomethylbenzene (MECAM). Examples of representative chelators and chelating groups are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, each of which is hereby incorporated by reference in its entirety.

In some embodiments, the metal chelator comprises desferrioxamine (also referred to as deferoxamine, desferrioxamine B, desferoxamine B, DFO-B, DFOA, DFB or desferal) or a derivative thereof. See, for example U.S. Pat. Nos. 8,309,583, 4,684,482, and 5,268,165, each of which is hereby incorporated by reference in its entirety for its teaching of desferrioxamine and desferrioxamine derivatives.

As is well known in the art, metal chelators can be specific for particular metal ions. Suitable metal chelators can be selected for incorporation into the biomolecule based on the desired metal ion and intended use of the biomolecule.

Paramagnetic ions form a magnetic moment upon the application of an external magnetic field thereto. Magnetization is not retained in the absence of an externally applied magnetic field because thermal motion causes the spin of unpaired electrons to become randomly oriented in the absence of an external magnetic field. By taking advantage of its property of shortening the magnetic relaxation time of water molecules, a paramagnetic substance is usable as an active component of MRI contrast agents. Suitable paramagnetic transition metal ions include $Cr^{3+}$, $Co^{2+}$, $Mn^{2+}$, $Ni^{2+}$, $Fe^{2+}$, $Fe^{3+}$, $Zr^{4+}$, $Cu^{2+}$, and $Cu^{3+}$. In preferred embodiments, the paramagnetic ion is a lanthanide ion (e.g., $La^{3+}$, $Gd^{3+}$, $Ce^{3+}$, $Tb^{3+}$, $Pr^{3+}$, $Dy^{3+}$, $Nd^{3+}$, $Ho^{3+}$, $Pm^{3+}$, $Er^{3+}$, $Sm^{3+}$, $Tm^{3+}$, $Eu^{3+}$, $Yb^{3+}$, or $Lu^{3+}$). In MRI, especially preferred metal ions are $Gd^{3+}$, $Mn^{2+}$, $Fe^{3+}$, and $Eu^{2+}$.

Suitable radionuclides include $^{99m}Tc$, $^{67}Ga$, $^{68}Ga$, $^{66}Ga$, $^{47}Sc$, $^{51}Cr$, $^{167}Tm$, $^{141}Ce$, $^{111}In$, $^{18}F$, $^{11}C$, $^{15}N$, $^{17}O$, $^{168}Yb$, $^{175}Yb$, $^{140}La$, $^{90}Y$, $^{88}Y$, $^{86}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{225}Ac$, $^{211}At$, $^{105}Rh$, $^{109}Pd$, $^{117m}Sn$, $^{149}Pm$, $^{161}Tb$, $^{177}Lu$, $^{198}Au$, $^{199}Au$, $^{89}Zr$, and oxides or nitrides thereof. The choice of isotope will be determined based on the desired therapeutic or diagnostic application. For example, for diagnostic purposes (e.g., to diagnose and monitor therapeutic progress in primary tumors and metastases), suitable radionuclides include $^{64}Cu$, $^{67}Ga$, $^{68}Ga$, $^{66}Ga$, $^{99m}Tc$, and $^{111}In$, $^{18}F$, $^{89}Zr$, $^{123}I$, $^{131}I$, $^{124}I$, $^{177}Lu$, $^{15}N$, $^{17}O$. For therapeutic purposes (e.g., to provide radiotherapy for primary tumors and metastasis related to cancers of the prostate, breast, lung, etc.), suitable radionuclides include $^{64}Cu$, $^{90}Y$, $^{105}Rh$, $^{111}In$, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, $^{199}Au$, $^{131}I$, and $^{125}I$, $^{212}Bi$, and $^{211}At$.

In some embodiments, the oxidatively unstable moiety can comprise a chromophore or fluorophore. In particular, fluorescence imaging has emerged with unique capabilities for molecular cancer imaging. Fluorophores emit energy throughout the visible spectrum; however, the best spectrum for in vivo imaging is in the near-infrared (NIR) region (650 nm-900 nm). Unlike the visible light spectrum (400-650 nm), in the NIR region, light scattering decreases and photo absorption by hemoglobin and water diminishes, leading to deeper tissue penetration of light. Furthermore, tissue autofluorescence is low in the NIR spectra, which allows for a high signal to noise ratio. There is a range of small molecule organic fluorophores with excitation and emission spectra in the NIR region. Some, such as indocyanine green (ICG) and cyanine derivatives Cy5.5 and Cy7, have been used in imaging for a relatively long time. Modern fluorophores are developed by various biotechnology companies and include: Li-COr dyes; IR-800 CW; IR-800 Mal; Alexa dyes; IRDye dyes; VivoTag dyes and HylitePlus dyes. Other examples of fluorescent dyes include, but are not limited to, Acridine Orange, Acridine Yellow, an Alexa Fluor dye, an Attodye, a BODIPY dye, Cascade Blue, coelenterazine, coumarin, a dansyl dye, 4',6-diamidino-2-phenylindole (DAPI), erythrosin, FLUO 3, fluorescein, FURA 2, 5-hydroxytryptamine (HAT), a Hoechst dye, INDO 1, JC-1 dye, Lucifer Yellow, Nile Red, Oregon Green dye, propidium iodide, QUIN 2, a rhodamine dye, R-phycoerythrin, R-phycoerythrin-Texas Red, SNARF, Texas Red, and cyanine dyes, such as Cy2, Cy3, Cy3.5, Cy5, Cy5.5, or Cy7. Many dyes described herein are photoswitchable dyes.

Additional examples include Dronpa, bsDronpa, Eos, enhanced yellow fluorescent protein (EYFP), red cyanine dyes, Cy5/Alexa 647, and rhodamine and oxazine dyes. Other useful dyes and techniques are described in U.S. Patent Publication No. 2005/0277197 (Chandler et al.). In general, the molecular weights of these fluorophores and chromophores are below 1 kDa.

By way of non-limiting illustration, examples of certain embodiments of the present disclosure are given below.

EXAMPLES

Example 1: Non-Radioactive Iodide Labeling of Cyclo Arg-Gly-Asp-d-Tyr-Lys (cRGDyK)

Figure 2:
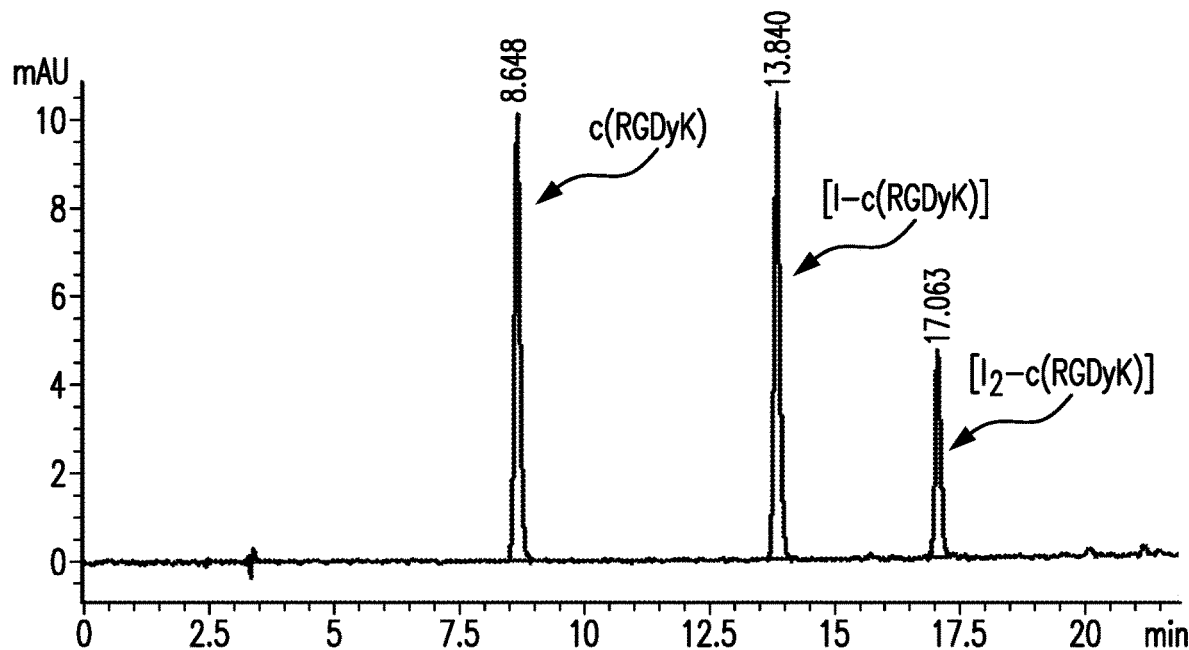
FIG. 2 illustrates a representative reverse-phase HPLC chromatogram post-labeling of cRGDyK (cyclo Arg-Gly-Asp-d-Tyr-Lys).
Figure 3:
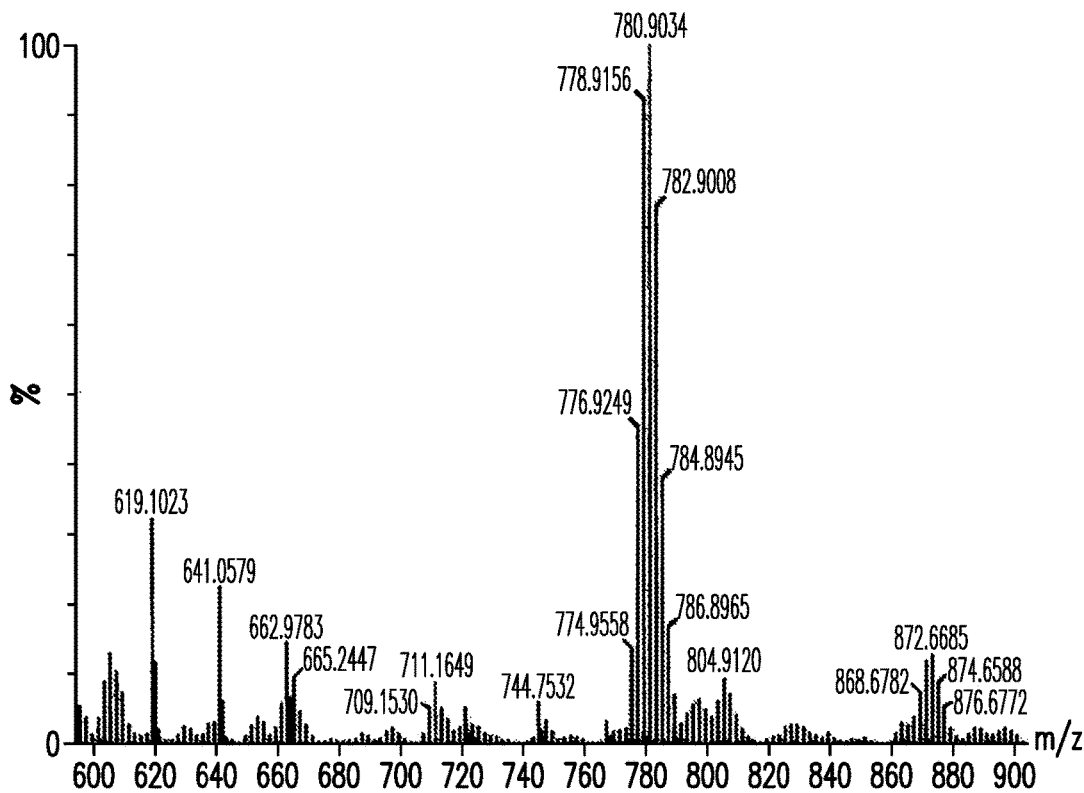
FIG. 3 illustrates the mass spectrum of a reaction mixture of cRGDyK (cyclo Arg-Gly-Asp-d-Tyr-Lys) and sodium iodide after incubation in an Iodogen tube for one hour.

Various conditions, including a varied ratio of reagents and incubation times, were investigated for non-radioactive labeling of cyclo Arg-Gly-Asp-d-Tyr-Lys (cRGDyK, FIG. 1) using Iodogen. For example, several experiments were performed in which cRGDyK to NaI ratio and incubation times were varied in the range of 39 to 100 and 30 to 60 minutes, respectively. Unreacted sodium iodide was removed from the reaction mixture by using a Sep-PaK $C_{18}$ Light Cartridge and the purified material was analyzed by an HPLC method. In each case peaks related to unreacted cRGDyK, mono-(I-RGDyK) and di-iodinated (I2-RGDyK) in variable amounts were seen in the HPLC chromatograms. The retention times for these peaks were determined as 8.6, 13.8, and 17.1 minutes for cRGDyK, I-cRGDyK, and $I_2$-cRGDyK, respectively (FIG. 2). Moreover, a reaction mixture from one of the experiments in which 1.6 µmol of cRGDyK and 62 µmol of Sodium Iodide (RGDyK:NaI ratio being 1:40) was incubated for 60 minutes and was analyzed by ESI mass spectral analysis. The ESI MS showed a peak at 780.9 (m/z) suggesting the formation of N-chloro derivative of mono iodinated cRGDyK (calculated m+H peak at 781.14; FIG. 3).

Example 2: Radiolabeling of Tyrosine Residues Using Chloramines

Preparation of Mono Chloramine from Ammonium Hydroxide and Sodium Hypochlorite

Stock solutions of sodium hypochlorite and ammonium hydroxide were prepared by diluting concentrated solutions of the two reagents as received. The concentration of the diluted sodium hypochlorite solution was determined by measured absorbance of the solution at 294 nm and extinction coefficient (350 $M^{-1}cm^{-1}$). Five milliliters of sodium hypochlorite solution (8.1 mM) were added dropwise to five milliliters of stirred solution of ammonium hydroxide (10 mM) in a beaker to form a solution of mono chloramine (NH$_2$Cl). The concentration of the mono chloramine solution was determined from the measured absorbance of the solution at 244 nm and extinction coefficient (461 M$^{-1}$cm$^{-1}$) and the NH$_2$Cl solution was used for non-radioactive and radio labeling of tyrosine, peptides, and proteins.

$^{125}$I Labeling of Tyrosine

A known amount of tyrosine amino acid (1.05 μ mole) in PBS (pH7.4) was added to a 1.5 mL polypropylene tube containing 0.5 mL phosphate buffer (0.1 M, pH 7.4). Career free $^{125}$INa (~50 μCi) followed by 1.5 μ mole mono chloramine solution in phosphate buffer were added to the tube. The reaction mixture was agitated and mixed with the pipette after each addition of the reagents. The reaction mixture was incubated at room temperature for 15 minutes. The radiolabeling reaction was quenched by addition of 0.125 mL of 10 mM sodium bisulfite solution in PBS (pH 7.4). Unreacted $^{125}$INaI was removed from the reaction mixture by using a conditioned Sep-Pak C$_{18}$ Light cartridge. The cartridge was washed with 1.5 mL water and followed by eluting with several 100 μL portions of ethanol. Each fraction was analyzed for total radioactivity by a dose calibrator. Efficiency of radiolabeling was calculated as 100%. The sample containing most of the activity was analyzed by using a RP-HPLC method. Two peaks at retention times 10.1 (7.7%) and 18.6 (92.3%) minutes were observed by the radioisotope detector.

Preparation of Non-Radioactive Iodinated Cyclo Arg-Gly-Asp-d-Tyr-Lys (cRGDyK)

In a non-radioactive labeling experiment, 3.2 μ mole cRGDyK and 1.28 μ mole Sodium Iodide were mixed in a small glass vial containing 0.5 mL Sodium Phosphate buffer (0.1 M, pH 7.4). A known amount of mono chloramine (3.17 μ mole) solution was added to the vial. The reaction mixture was mixed well and incubated at room temperature for 30 minute. At the end of the incubation time, the non-radioactive labeling reaction was quenched by the addition of a reducing agent, sodium bisulfite (0.4 mL of ~10 mM NaHSO$_3$ solution). The crude reaction mixture was analyzed by a Reversed-Phase HPLC method. The chromatographic method involving a Zorbax C18 5 μm, 4.6×250 mm column, flow rate of 1 mL/min, and UV detection at λ=280 nm, and a gradient mobile phase was used. The following gradient of water containing 0.1% TFA (A) and acetonitrile containing 0.1% TFA (B) were used: the gradient system began at 95% A and 5% B followed by ramping the concentration of B to 75% in 30 minutes. At the end of this period the concentration of B was brought down to 5% in one minute and kept up to 35 minutes. Three peaks (percentages given in the parenthesis at 7.2 (44.48% due to excess unreacted cRGDyK used), 9.5 (44.7), and 10.9 (2.1) minutes were seen in the HPLC. The ratio of I-cRGDyK and I$_2$-cRGDyK formed are 94.3 and 5.7%, respectively. An ESI mass spectral analysis of the 9.5 minutes peak showed a m+H peak at 746.1 vs. calculated mass for I-cRGDyK as 745.6.

$^{125}$I Labeling of Cyclo Arg-Gly-Asp-d-Tyr-Lys (cRGDyK)

For $^{125}$I labeling of cyclo Arg-Gly-Asp-d-Tyr-Lys (cRGDyK), a known amount of the peptide (1.28 μ mole) in PBS (pH7.4) was added to a 1.5 mL polypropylene tube containing 0.5 mL phosphate buffer (0.1M, pH 7.4). Career free $^{125}$INa (89 μCi) followed by mono chloramine (2.0 μ mole) in phosphate buffer (pH 7.4) were added to the tube. The reaction mixture was agitated and mixed with the pipette after addition of each reagent and the reaction mixture was incubated at room temperature for 10 minutes. Unreacted $^{125}$INaI was removed from the reaction mixture using a conditioned Sep-Pak C$_{18}$ Light cartridge. The cartridge was washed with 1.5 mL water and followed by several 100 μL portions of 0.5 mL ethanol. Each fraction was analyzed for total radioactivity by a dose calibrator. Efficiency of radiolabeling was calculated as, 96.9%. The sample was analyzed by a Reversed-Phase HPLC method. Two peaks at 9.5 minutes and 10.3 minutes with 90% and 10% peak areas in the radioisotope detector corresponding to $^{125}$I-cRGDyK and $^{125}$I$_2$-cRGDyK were observed in the HPLC.

$^{125}$I Radiolabeling of Bovine Serum Albumin (BSA)

A sample of Bovine Serum Albumin (BSA) was radiolabeled with $^{125}$I by transferring 50 μg the BSA sample into an Eppendorf tube containing 100 μL of sodium phosphate buffer (0.1 M pH 7.4). Career free $^{125}$INa (~93 μCi) followed by mono chloramine (0.8 μ mole) in phosphate buffer (pH 7.4) were added to the tube. The reaction mixture was agitated and mixed with the pipette after addition of each reagent and the reaction mixture was incubated for 30 min at room temperature. The reaction was quenched by addition of 0.1 mL of 10 mM Sodium Bisulfite. The crude reaction mixture was purified using a Sephadex G-25 or PD-10 column. An efficiency for radiolabeling or incorporation of $^{125}$I was calculated as 82.4%. The radiolabeled BSA sample was analyzed for free $^{125}$I by using a Paper Chromatography and for purity by Size-Exclusion Chromatography methods. Both methods gave >98% purity.

$^{125}$I Radiolabeling of a Antibody Fragment, 3E8. G4S Dibody

An antibody fragment (3E8.G4S) with weighted average molecular weight of 68 kD was radiolabeled with $^{125}$I. A 50 μg of the antibody fragment, 3E8.G4S, was transferred into an Eppendorf tube containing 100 μL of sodium phosphate buffer (0.1 M pH 7.4). Career free $^{125}$INa (~113 μCi) followed by mono chloramine (0.8 mole) in phosphate buffer (pH 7.4) were added to the tube. The reaction mixture was agitated and mixed with the pipette after addition of each reagent. The reaction mixture was incubated at room temperature for 10 min and the reaction was quenched by adding 100 uL of 10 mM Sodium Bisulfite. The crude reaction mixture was purified using a conditioned Sephadex G-25 or PD-10 column. The incorporation of $^{125}$I was calculated as 81.4%. The purified material was analyzed by a paper chromatographic method for the presence of free $^{125}$I. The free iodine was found <1% with 99% bound to the antibody fragment. The Size-Exclusion Chromatography (SCE) using an Agilent SEC-3 100 A column (4.6×300 mm) showed a peak for radiolabeled 3E8.G4S at 6.7 minutes with no evidence of free $^{125}$I.

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative components and method steps disclosed herein are specifically described, other combinations of the components and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A method for iodinating a biomolecule, the method comprising;
   providing a biomolecule comprising a tyrosine residue; and
   reacting the biomolecule with a chloramine and an iodine source under conditions effective to form an iodinated biomolecule without forming N-chloro derivatives, wherein the iodinated biomolecule comprises an iodinated tyrosine residue,
   wherein the chloramine is selected from an alkylchloroamine, monochloramine, dichloramine, trichloramine, or a combination thereof.

2. The method of claim 1, wherein the chloramine has a molar mass of less than 250 g/mol.

3. The method of claim 1, wherein the chloramine comprises an alkylchloramine.

4. The method of claim 3, wherein the alkylchloramine is chosen from methylchloramine, dimethylchloramine, ethylchloramine, diethylchloramine, or a combination thereof.

5. The method of claim 1, wherein the chloramine is chosen from monochloramine, dichloramine, trichloramine, or a combination thereof.

6. The method of claim 1, wherein the iodine source comprises an iodide salt.

7. The method of claim 6, wherein the iodide salt is chosen from [$^{123}$I] NaI, [$^{124}$I] NaI, [$^{125}$I] NaI, [$^{131}$I] NaI, [$^{123}$I] KI, [$^{124}$I] KI, [$^{125}$I] KI, and [$^{131}$I] KI.

8. The method of claim 1, wherein the iodinated tyrosine residue is defined by the Formula IA or Formula IB below

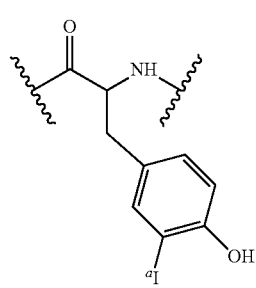

Formula IA

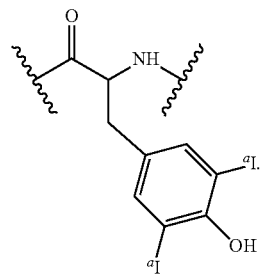

Formula IB wherein $^{a}$I is chosen from $^{123}$I, $^{124}$I, $^{125}$I, and $^{131}$I.

9. The method of claim 1, wherein the biomolecule is defined by the formula below

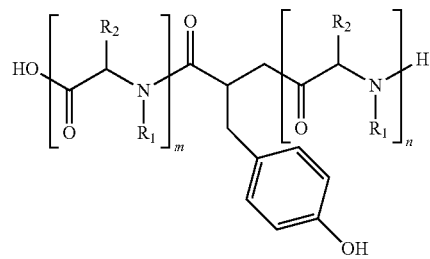

and the iodinated biomolecule is defined by Formula IIA or Formula IIB below

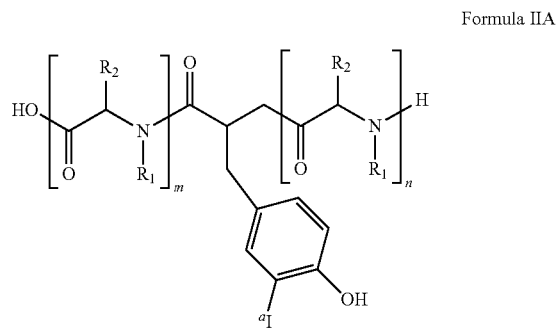

Formula IIA

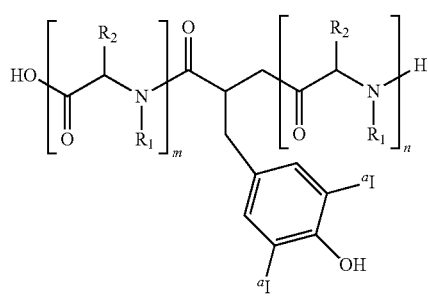

Formula IIB wherein
   m is an integer from 0 to 150 and n is an integer from 0 to 150, with the proviso that at least one of m and n is not 0; and
   independently for each occurrence in the polypeptide, $R_1$ is H and $R_2$ is selected from one of the following

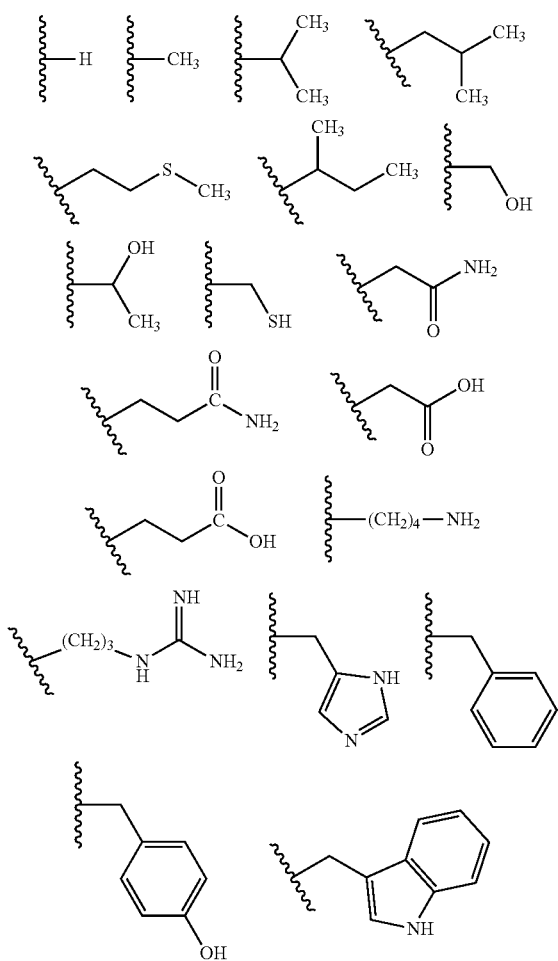

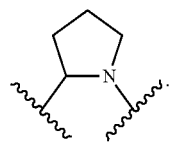 [SMILES: *C1CCCN1*]

wherein $^aI$ is chosen from $^{123}I$, $^{124}I$, $^{125}I$, and $^{131}I$.

10. The method of claim 1, wherein the biomolecule comprises an antibody or antibody fragment.

11. The method of claim 1, wherein the biomolecule further comprises an oxidatively unstable moiety.

12. The method of claim 11, wherein the oxidatively unstable moiety comprises a conjugated moiety, a chromophore or fluorophore, a metal chelator, or any combination thereof.

13. The method of claim 1, wherein the chloramine is formed from reacting ammonia or an alkylamine with hypochlorite under conditions effective to form the chloramine, and wherein the molar ratio of the ammonia or alkylamine and the hypochlorite is from 0.8:1 to 3:1.

14. The method of claim 1, wherein the method comprises reacting the biomolecule with a chloramine and an iodine source under conditions effective to form an iodinated biomolecule without adversely impacting the biomolecule.

15. A method for iodinating a biomolecule, the method comprising;
providing a biomolecule comprising a tyrosine residue; and
reacting the biomolecule with a chloramine and an iodine source under conditions effective to form an iodinated biomolecule, wherein the iodinated biomolecule comprises an iodinated tyrosine residue,
wherein the chloramine is selected from an alkylchloroamine, monochloramine, dichloramine, trichloramine, or a combination thereof;
wherein the biomolecule comprises an oxidatively unstable moiety, and wherein the oxidatively unstable moiety remains intact following the reacting step such that the iodinated biomolecule also includes the oxidatively unstable moiety.

or $R_1$ and $R_2$, together with the atoms to which they are attached, form a five-membered heterocycle defined by the structure below

* * * * *